(12) United States Patent
Van Giezen et al.

(10) Patent No.: US 6,395,946 B1
(45) Date of Patent: May 28, 2002

(54) PROCESS FOR THE PREPARATION OF STYRENES

(75) Inventors: Joseph Cornelis Van Giezen; Jean-Paul Lange; Carolus Matthias Anna Maria Mesters, all of Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/622,275

(22) PCT Filed: Feb. 16, 1999

(86) PCT No.: PCT/EP99/01005

§ 371 (c)(1), (2), (4) Date: Aug. 14, 2000

(87) PCT Pub. No.: WO99/42425

PCT Pub. Date: Aug. 26, 1999

(30) Foreign Application Priority Data

Feb. 18, 1998 (EP) ............................................. 98200513

(51) Int. Cl.⁷ ................................................. C07C 1/20
(52) U.S. Cl. ........................ 585/437; 585/435; 585/436; 585/469
(58) Field of Search ................................ 585/435, 436, 585/437, 469

(56) References Cited

FOREIGN PATENT DOCUMENTS

GB 2176801 1/1987

OTHER PUBLICATIONS

Takahashi et al, The Canadian Journal of Chemical Engrg. vol. 66, Jun. 1988, pp. 433–437.

61/72727 + (Abst) JP Apr. 14, 1986.

*Primary Examiner*—Walter D. Griffin

(57) ABSTRACT

Styrene or substituted styrenes are produced by a process comprising the gas phase dehydration of 1-phenyl ethanol or substituted 1-phenyl ethanol in the presence of a solid acidic catalyst comprising a zeolite and a binder material, wherein the weight ratio of zeolite to binder is in the range of from 1:99 to 90:10 and wherein the following relation applies: $0<K<5$ with $K=V/S\times[(Pz\times fz)+(Pb\times fb)]^{1/2}$, wherein: V/S is the volume/surface ratio of the catalyst used in mm; fz is the weight fraction of zeolite present in the catalyst in grams zeolite per gram catalyst; fb is the weight fraction of binder present in the catalyst in grams binder per gram catalyst; pz is the intrinsic productivity of zeolite expressed as grams styrene produced per gram of the zeolite per hour, as measured for pure zeolite samples of small particle size (i.e., <0.1 mm) at the temperature applied in gas phase dehydration and at a conversion of 1-phenyl ethanol into styrene below 80%; and Pb is the intrinsic productivity of the binder expressed as grams styrene produced per gram of binder per hour, as measured for pure binder samples of small particle size (i.e., <0.1 mm) under the same conditions as used for determining Pz.

10 Claims, No Drawings

PROCESS FOR THE PREPARATION OF STYRENES

The present invention relates to a process for the preparation of styrene or substituted styrenes, more specifically to such a process comprising the gas phase dehydration of 1-phenyl ethanol or substituted 1-phenyl ethanols.

Within the further context of the present application the term "substituted styrenes" refers to vinyl aromatic compounds of the general formula $$Ar\text{—}CR\text{=}CH_2,$$

wherein Ar is a phenyl, tolyl or xylyl group and R is H or a methyl group. When referring to "styrene" in the present application, these substituted styrenes are also included, unless indicated otherwise. Similarly, the term "substituted 1-phenyl ethanols" refers to aromatic alcohols of the general formula $$Ar\text{—}C(R)(CH_3)\text{—}OH$$

wherein Ar and R are as defined above. When referring to "1-phenyl ethanol", these substituted 1-phenyl ethanols are also included, unless indicated otherwise.

A commonly known method for manufacturing styrene is the coproduction of propylene oxide and styrene starting from ethylbenzene (a Styrene Monomer/Propylene Oxide or SM/PO process). In general such process involves the steps of (i) reacting ethylbenzene with oxygen or air to form ethylbenzene hydroperoxide, (ii) reacting the ethylbenzene hydroperoxide thus obtained with propene in the presence of an epoxidation catalyst to yield propylene oxide and 1-phenyl ethanol, and (iii) converting the 1-phenyl ethanol into styrene by dehydration using a suitable dehydration catalyst. The present invention particularly focuses on the last step, i.e. the dehydration of 1-phenyl ethanol to yield styrene.

Step (iii) of the process described above, i.e. the production of styrene by dehydrating 1-phenyl ethanol, can be carried out in different ways as is well known in the art. In general, the dehydration can be carried out in the gas phase or in the liquid phase in the presence of a dehydration catalyst. Suitable dehydration catalysts are known and include for instance acidic materials like alumina, alkali alumina, aluminium silicates and H-type synthetic zeolites. Dehydration conditions are also well known and usually include reaction temperatures of 50–205° C., typically 100–200° C., for liquid phase dehydration and 210–320° C., typically 280–310° C., for gas phase dehydration. Pressures usually range from 0.1 to 10 bar.

In GB-A-2,176,801 the liquid-phase dehydration of an aromatic alcohol into an aromatic vinyl compound is described, wherein the dehydration is carried out at elevated temperature in the presence of a solid acid catalyst. Aluminium silicate and H-type synthetic zeolites are mentioned as suitable catalysts, but no further details as to the properties of these materials is given.

In Takahashi et al., The Canadian Journal of Chemical Engineering, Sol. 66, June 1988, pp. 433–437, a process for the liquid phase dehydration of 1-phenyl ethanol into styrene is described using various types of acidic catalysts. The catalysts used include silica-alumina, Y type zeolites, mordenites, H-ZSM-5 and several aluminas, all used in the form of crushed particles of 24–32 mesh (corresponding with 0.5 to 0.7 mm). This publication concludes that when the concentration of effective acid sites on the catalyst increases, the dehydration reaction rate increases, but the styrene selectivity decreases. A certain alumina catalyst was found to provide the best balance between reaction rate and styrene selectivity.

In JP-A-61/72727 the gas-phase dehydration of 1-phenyl ethanol into styrene is described, wherein a zeolite is used as the dehydration catalyst. The patent application does not give any further details as to the types and properties of suitable zeolites, except that in the working examples OSZ-250, a H-Y-type zeolite, is used in the form of crushed particles having a size of 32–60 mesh (corresponding with 0.25–0.50 mm). In the working example the feed solely consisted of 1-phenyl ethanol without other compounds being present.

The present invention aims to provide an effective dehydration process for converting 1-phenyl ethanol into styrene, which process can also be used in the dehydration step of a commercial SM/PO process. In such a process the feed to the dehydration section will not only contain 1-phenyl ethanol, but also substantial amounts of other compounds formed in the preceding sections. Examples of such compounds are 2-phenyl ethanol, methyl phenyl ketone, some styrene monomer, ethylbenzene and water.

It has been found that 1-phenyl ethanol either as such or in a process stream in an SM/PO process can be very effectively converted into styrene in a gas phase dehydration process by selecting a zeolitic catalyst meeting certain specific requirements.

Accordingly, the present invention relates to a process for the preparation of styrene or substituted styrenes comprising the gas phase dehydration of 1-phenyl ethanol or substituted 1-phenyl ethanol in the presence of a solid acidic catalyst comprising a zeolite and a binder material, wherein weight ratio of zeolite to binder is in the range of from 1:99 to 90:10 and wherein the following relation applies:

$$0 < K < 5 \tag{1}$$

with:

$$K = V/S * [(Pz*fz)+(Pb*fb)]^{1/2} \tag{2}$$

wherein:

V/S is the volume/surface ratio of the catalyst used in mm;

fz is the weight fraction of zeolite present in the catalyst in grams zeolite per gram catalyst;

fb is the weight fraction of binder present in the catalyst in grams binder per gram catalyst;

Pz is the intrinsic productivity of the zeolite expressed as grams styrene produced per gram of zeolite per hour, as measured for pure zeolite samples of small particle size (i.e. <0.1 mm) at the temperature applied in gas phase dehydration and at a conversion of 1-phenyl ethanol into styrene below 80%; and Pb is the intrinsic productivity of the binder expressed as grams styrene produced per gram of binder per hour, as measured for pure binder samples of small particle size (i.e. <0.1 mm) under the same conditions as used for determining Pz.

The catalyst to be used comprises zeolite and binder in a weight ratio of zeolite to binder of from 1:99 to 90:10, preferably of from 3:97 to 35:65. Suitable binder materials include inorganic oxides like silica, alumina, boria, zirconia, titania and silica-alumina as well as organic materials like carbon or polymers. Of these, the substantially inert binder materials silica and alumina are preferred. The zeolite to be used in principle may be any zeolite having sufficient acidity to catalyse the dehydration of 1-phenyl ethanol. Suitable zeolites, then, include H-ZSM-5, H-ZSM-23, H-mordenite, H-Y-zeolite and beta-zeolite, but also silica-alumina phosphate molecular sieve materials, such as SAPO-34. However, other acidic zeolitic materials may be applied as well.

The catalyst to be used must meet very specific requirements as regards particle size, outer surface and zeolite content. These requirements are summarised in equations (1) and (2):

$$0<K<5 \quad (1)$$

with:

$$K=V/S*[(Pz*fz)+(Pb*fb)]^{1/2} \quad (2)$$

wherein V/S, Pz, Pb, fz and fb have the meaning as indicated above. The quotient of volume V (in mm$^3$) and outer surface S (in mm$^2$) is expressed in mm and is a measure for the particle size and its shape. For spherical catalyst particles, V/S is ⅙ of the particle diameter. For cylindrical catalyst particles V/S is ¼ of the particle diameter. For catalyst particles shaped as trilobes, stars, quadrulobes, wokkels and the like, the ratio V/S will be smaller than ¼ of the outer diameter of the enclosing cylinder. It has been found advantageous to select V/S, Pz, Fb, fz and fb such that K has a value of less than 2, preferably of less than 0.5 and most preferably of less than 0.2.

The weight fractions of zeolite (fz) and binder (fb) indicate the amounts of zeolite and binder in grams per gram of catalyst. The sum of fz and fb is equal to 1, i.e. the catalyst consists of zeolite and binder. The productivities Pz and Pb in fact indicate the dehydration activity of the pure zeolite and pure binder, respectively. For the purpose of the present invention it is preferred that the binder is substantially inert, so that Pb=0. As a result, the following relation applies:

$$K=V/S*(Pz*fz)^{1/2} \quad (3)$$

The conditions under which the dehydration is carried out may vary within wide limits, but should anyhow be such that the 1-phenyl ethanol is in the gas phase. At atmospheric pressure this implies that the reaction temperature should be higher than the boiling temperature of 1-phenyl ethanol, which is 203–204° C. At subatmospheric conditions, however, the reaction temperature may be lower. In general, the gas phase dehydration is suitably carried out at a temperature in the range of from 205 to 300° C., preferably 210 to 250° C., at a pressure of from 0.5 to 5 bar.

The process according to the present invention can be carried out in different operational modes in terms of the way in which the catalyst is used. In one embodiment of the present invention the catalyst is used in the form of particles having an average particle size of at least 0.5 mm, preferably from 1 to 10 mm, more preferably from 1.5 to 5 mm, in a packed fixed bed. Such relatively large particle sizes are preferred to keep the pressure drop within the reactor at an acceptable level. In this mode of operation the catalyst particles are randomly packed into a bed over which the feed comprising 1-phenyl ethanol is passed upwardly or downwardly. The catalyst particles may have any desired shape including spherical, (hollow) cylindrical, trilobe, star-shaped, pellet-shaped etc. In another embodiment of the present invention the catalyst is used in the form of particles having an average particle size of 0.5 mm or less, preferably from 0.02 to 0.1 mm, in a fluidised bed. In this mode of operation spherical catalyst particles are normally applied, so that the ratio V/S equals ⅙ of the diameter of the catalyst particles. Since the catalyst particles are free flowing and hence are exposed to relatively severe mechanical forces, a certain minimum amount of binder material should be present to give the catalyst particles sufficient strength. Preferred binder contents are 20% by weight or more, more preferably at least 30% by weight. The gaseous feed enters the fluidised bed reactor at the bottom at a certain velocity, thus helping to keep the catalyst bed in its fluidised state, and the styrene-containing product leaves the reactor at the top.

In a still further embodiment of the present invention the catalyst is applied as a layered catalyst, which is as a thin layer on either small support particles or on a monolithic support or a structured packing. In these forms the catalyst is most suitably applied in a fixed bed operation. The coated catalyst particles, however, could also be applied in a fluidised bed operation, if the particles are sufficiently small (i.e. <100 μm). In general, monolithic catalysts are continuous, unitary structures containing many narrow, parallel straight or zigzag passages. Catalytically active ingredients are distributed uniformly in a porous layer deposited on the walls of the channels in the monolithic structure. A frequently applied monolithic structure is the honeycomb structure. The essence of monolithic catalysts is the very thin layers, in which internal diffusion resistance is small. A structured packing is an open cross-flow structure, which can serve as a catalyst carrier by applying a thin layer of catalytically active material on the walls of the channels. Such structured packings are for instance available from Sulzer Chemtech. An example of a structured packing is a foam containing channels. For all layered catalysts (coated particles, monolithic supports and structured packings) the thickness of the applied catalyst layer will usually vary between 1 and 100 μm, more suitably 1 and 50 μm. The V/S ratio in this case will be about equal to the layer thickness assuming that the half of the total surface bound to the support is not accessible for the reactant gas.

The invention is further illustrated by the following example without restricting the scope of the invention to the particular embodiments illustrated in this example.

EXAMPLE

The experiments were carried out in a stainless steel reactor (13 mm internal diameter; 30 cm length) equipped with an internal thermowell (0.5 outer diameter). The feed was passed downwardly through the reactor. The catalyst particles used were diluted with glass beads (2 mm diameter) prior to filling the central segment of the reactor. The feed line was traced to the reactor temperature to allow the feed to vaporise. The product was collected and analysed by means of gas chromatography. The feed consisted of:

82% by weight of 1-phenyl ethanol
  5% by weight 2-phenyl ethanol
  11% by weight methyl phenyl ketone
  1–2% by weight of water and
  the balance up to 100% by weight of styrene plus ethyl benzene.

The catalyst used was based on H-ZSM-5 zeolite, which was extruded with $SiO_2$ into trilobes of 1.6 mm outer diameter. Two batches were prepared: one with 20% by weight zeolite and one with 80% by weight zeolite. The extruded catalyst was also tested in the form of crushed particles of about 0.2 mm.

The reactor was loaded with a sufficient amount of catalyst to have about 0.5 grams of zeolite in the reactor. The catalyst was heated under a flow of nitrogen, initially rapidly up to 80° C., then within 2 hours to 120° C. and subsequently rapidly up to the reaction temperature of 220° C., at which temperature the catalyst was kept for 2 hours. Then, the feed was introduced into the reactor and the catalyst was contacted with the vaporised feed at a rate of 18 g/h (corresponding with a weight hourly space velocity of 30 grams 1-phenyl ethanol per gram zeolite per hour) and atmospheric pressure for several days.

The productivity Pz of the zeolite was determined by running the pure zeolite powder diluted in glass beads at 220° C. and at a 1-phenyl ethanol conversion of approximately 55%. The Pz had a value of 5 g styrene/g zeolite/h.

The results are indicated in Table I. The abbreviations D, Conv. and Sel. refer to catalyst particle diameter, conversion and selectivity, respectively. The conversion is calculated on the basis of the carbon content C of the feed and of the unconverted feed leaving the reactor:

$$\text{Conversion} = \frac{C(\text{feed}) - C(\text{unconverted feed})}{C(\text{feed})} \times 100\%$$

The carbon content of the unconverted feed is the difference between the total carbon content of the product stream that leaves the reactor and the C of the styrene formed.

The selectivity is calculated on the basis of the carbon content of the styrene formed and the carbon content of the feed:

$$\text{Selectivity} = \frac{C(\text{styrene})}{C(\text{feed})} \times 100\%$$

TABLE I

Results

| Run No. | D (mm) | fz (g/g) | V/S (mm) | K | Time (h) | Conv. (%) | Sel. (%) |
|---|---|---|---|---|---|---|---|
| 1 | 0.2 | 0.2 | 0.033 | 0.03 | 5 | 95 | 98 |
|   |     |     |       |      | 50 | 92 | 97 |
|   |     |     |       |      | 100 | 90 | 98 |
| 2 | 0.2 | 0.6 | 0.033 | 0.05 | 5 | 95 | 90 |
|   |     |     |       |      | 50 | 85 | 93 |
|   |     |     |       |      | 100 | 81 | 92 |
| 3 | 1.6 | 0.2 | 0.400 | 0.38 | 5 | 95 | 95 |
|   |     |     |       |      | 50 | 80 | 94 |
|   |     |     |       |      | 100 | 65 | 92 |
| 4 | 1.6 | 0.6 | 0.400 | 0.66 | 5 | 60 | 75 |
|   |     |     |       |      | 50 | 52 | 80 |
|   |     |     |       |      | 100 | 45 | 82 |

From Table I it can be seen that the selectivity is high and stable for catalysts having a K of less than 0.5 (runs Nos. 1–3). The catalyst with a K of more than 0.5 is still performing adequately, but shows a somewhat lower selectivity which is also less stable. The conversion for the catalysts used in runs Nos. 1–3 is also somewhat higher than the conversion for the catalyst used in run No. 4, although the latter is still sufficiently high.

Comparative Example

Run No. 3 was repeated, but with a liquid in stead of a vaporous feed. Two runs of 48 hours each were carried out, one at 120° C. (run No. 5) and one at 170° C. (run No. 6), at a space velocity of 10 g 1-phenyl ethanol/g zeolite/h.

It was found that in both runs the conversion was higher than 80%, but the selectivity did not exceed 30% (run No. 5) and 50% (run No. 6).

Hence, the comparative examples demonstrate that the process according to the present invention must be a gas phase process.

What is claimed is:

1. Process for substituted styrenes comprising the gas phase dehydration of 1-phenyl ethanol or substituted 1-phenyl ethanol in the presence of a solid acidic catalyst comprising a zeolite and a binder material, wherein the weight ratio of zeolite to binder is in the range of from 1:99 to 90:10 and wherein the following relation applies:

$$0 < K < 5 \quad (1)$$

with:

$$K = V/S * [(Pz*fz) + (Pb*fb)]^{1/2} \quad (2)$$

wherein:

V/S is the volume/surface ratio of the catalyst used in mm;

fz is the weight fraction of zeolite present in the catalyst in grams zeolite per gram catalyst;

fb is the weight fraction of binder present in the catalyst in grams binder per gram catalyst;

Pz is the intrinsic productivity of the zeolite expressed in as grams styrene produced per gram of zeolite per hour, as measured for pure zeolite samples of small particle size at the temperature applied in the gas phase dehydration and at a coversion of 1-phenyl ethanol into styrene below 80%; and Pb is the intrinsic productivity of the binder expressed as grams styrene produced per gram of binder per hour, as measured for pure binder samples of small particle size under the same conditions as used for determining Pz.

2. Process according to claim 1, wherein K has a value between 0 and 2.

3. Process according to claim 1 wherein the intrinsic productivity of the binder, Pb, is essentially zero, so that:

$$K + V/S * (Pz*fz)^{1/2}$$

wherein V/S, Pz and fz are as defined in claim 1.

4. Process according to claim 2, wherein the weight ratio of zeolite to binder is in the range of from 3:97 to 35:65.

5. Process according to claim 4, wherein the binder is silica or alimina.

6. Process according to claim 1, wherein the temperature at which the gas phase dehydration is carried out is in the range of from 205 to 300° C., at a pressure of from 0.5 to 5 bar.

7. Process according to claim 1 wherein the zeolite is H-ZSM-5, H-ZSM-23, H-mordenite, H-Y-zeolite or a silica-alumina phosphate.

8. Process according to claim 1, wherein the catalyst is used in the form of particles having an average particle size of at least 0.5 mm in a packed fixed bed.

9. Process according to claim 4, wherein the catalyst is used in the form of particles having an average particle size of 0.5 mm or less and in a fluidized bed.

10. Process according to claim 4, wherein the catalyst is applied as a coating on a monolithic support or a structured packing in a fixed bed operation.

* * * * *